(12) United States Patent
Uda et al.

(10) Patent No.: US 6,452,671 B1
(45) Date of Patent: Sep. 17, 2002

(54) ILLUMINATOR FOR MACRO INSPECTION, MACRO INSPECTING APPARATUS AND MACRO INSPECTING METHOD

(75) Inventors: Mitsuru Uda; Tsuyoshi Yamaguchi; Masami Shinohara, all of Shiga-ken (JP)

(73) Assignee: International Business Machines Corporation, Armonk, NY (US)

( * ) Notice: Subject to any disclaimer, the term of this patent is extended or adjusted under 35 U.S.C. 154(b) by 28 days.

(21) Appl. No.: 09/698,423

(22) Filed: Oct. 27, 2000

(30) Foreign Application Priority Data

Oct. 29, 1999 (JP) .............................. 11-308766

(51) Int. Cl.[7] .............................................. G01N 21/00
(52) U.S. Cl. .................... 356/237.2; 356/237.5
(58) Field of Search .................. 356/237.1, 237.2, 356/237.3, 237.4, 237.5, 237.6, 394; 250/559.4, 559.44

(56) References Cited

U.S. PATENT DOCUMENTS

| 4,601,577 A | * | 7/1986 | Gotou et al. | 356/237 |
| 4,648,053 A | * | 3/1987 | Fridge | 356/551 |
| 5,367,174 A | * | 11/1994 | Bazile et al. | 356/237 |

* cited by examiner

*Primary Examiner*—Hoa Q. Pham
(74) *Attorney, Agent, or Firm*—Jay H. Anderson

(57) ABSTRACT

The inspecting apparatus according to the present invention includes an illuminator for emitting radiation onto a substrate having a surface on which a fine feature pattern is formed. Inspection for defects in the pattern is performed by visually inspecting radiation diffracted by the surface. The illuminator provides radiation including two different complementary colors.

20 Claims, 6 Drawing Sheets

ILLUMINATOR FOR MACRO INSPECTION, MACRO INSPECTING APPARATUS AND MACRO INSPECTING METHOD

FIELD OF THE INVENTION

The present invention relates to an illuminator for macro inspection, a macro inspecting apparatus, and a macro inspecting method. More particularly to an illuminator, an inspecting apparatus, and an inspecting method which are suitable for not only inspecting dust and scratches on the surface of a wafer, but also visually inspecting the presence or absence of deformed parts caused by local defocusing on the surface of a wafer, which is finely patterned by a photolithographic method.

DESCRIPTION OF RELATED ART

In a photolithographic process for producing a semiconductor device, various factors such as line width and superposition have to be controlled. In addition, other factors such as resist thickness also have to be controlled so as not to cause defocusing. In order to control these factors, visual inspection for defocusing, size measurement, and overlay measurement are conducted as an in-line inspection of a wafer after resist pattern is formed by each photomask. Generally, in size measurement and overlay measurement, measurement frequency can be reduced as far as photolithographic process is stable. Therefore, only sampling inspection can be conducted in these measurements.

However in a visual inspection for defocusing, all the lots are generally inspected. This is because the visual inspection (macro inspection) can detect deformations of resist patterns due to defocusing, which cannot be microscopically detected in the size measurement or overlay measurement. The term "defocusing" used herein means the phenomenon that deformation of resist patterns is caused by the resist being out of focus in stepper exposure. Such defocusing may be caused by foreign particles adhered onto the surface of a substrate such as a wafer, distortion or deficiencies such as scratches on the surface of the substrate, the difference in resist thickness applied on the surface of a substrate, and the like, which leads to the deformation of resist patterns.

If deformations of resist patterns are early detected, they are peeled off from a substrate, and then the substrate is subjected to a resist-applying step again, thus a commercially available product can be produced without affecting its properties. On the contrary, if visual inspection is not sufficiently effective, detection delay may cause unrenewable yielding loss over several lots.

Thus, visual inspection for defocusing has been quite important in producing semiconductor devices. However, it has also been quite difficult to detect defocusing. In the visual inspection for defocusing, micron-order lines of a resist pattern (finely patterned surface) function as a diffraction grating. When radiation is directed at the lines, normal parts and deformed parts in the resist pattern diffract the radiation differently, so that the color or brightness of diffracted radiation appears differently. However, since there are only slight differences in color and brightness between diffracted radiation, the difference between them is hard to discern. Thus, visual inspection has so far required much time and experience.

In order to solve the above problems, the Japanese unexamined Patent Publication (Patent Kokai) No. 63-305512, No. 62-127652, and No. 10-325805 disclose various automatic inspecting apparatuses. However, conventional halogen lamps are used in these apparatuses, so that light diffracted by a normal position cannot be clearly distinguished from light diffracted by a deformed position. Accordingly, even if light of a predetermined range of wavelength is separated from the diffracted light and then converted into electrical signal by an optoelectronic transducer, detection within a high degree of accuracy cannot be achieved because only a slight difference has to be detected.

The inventors of the present invention compared and evaluated various illuminators for inspection of photoprocessed semiconductor, and found that no illuminator can adequately detect defocusing.

An object of the present invention is to provide an illuminator for macro inspection, which may detect the presence or absence of defocusing problems on a surface of a semiconductor substrate such as wafer, on which resist patterns are finely formed.

Another object of the present invention is to provide an inspecting apparatus and method using the above illuminator.

SUMMARY OF THE INVENTION

In the illuminator for macro inspection according to the present invention, radiation is emitted at a predetermined angle from a light source to a surface of a substrate, on which predetermined patterns are formed, so as to determine the presence or absence of deformations on the patterned surface by visually inspecting radiation diffracted by the patterned surface. The emitted radiation may include two different, high color contrast radiation.

It is preferable that these two colors of high color contrast are complementary colors, but it is also acceptable that they are close to complementary colors. The illuminator for emitting radiation can be the one which emits radiation including two different high color contrast radiation from a single light source, or it can also be the one which emits two different high color contrast radiation separately from two different light sources. In addition, the illuminator may comprise two light sources and two kinds of filters for allowing two different high color contrast radiation to separately pass through. Alternatively, the illuminator may comprise one light source and a filter for allowing radiation including two different high color contrast radiation to pass through. Thus, the illuminator can be configured variously.

Two colors of high color contrast, especially complementary colors, produce a sharper contrast than any other combination of two colors, so that glaring and sharp impression is given to human eyes. Examples of complementary color pairs include red and blue green, yellow and blue, green and brown, and the like. Most preferable pair is red and blue green in terms of contrast effect. Two colors of high color contrast include not only complementary colors, but also a combination of two colors close to complementary colors and two colors which produce a sharp contrast in combination. ("two colors of high color contrast" is hereinafter referred to as "complementary colors" unless otherwise specified.)

The radiation applied to the substrate by the illuminator can be obtained as synthesized radiation including two different complementary-color radiation emitted from a single light source. As such an illuminator, it is preferable to use a halogen lamp having a color temperature of 1500K to 3500K and including red light with a wavelength of 677 nm and blue green light with a wavelength of 495 nm. Particularly, a halogen lamp having a color temperature of 2200K is preferable. In addition, an illuminator preferably comprises a yellow filter, as yellow is a color obtained by combining red and blue green.

Alternatively, the radiation applied to the substrate by the illuminator can be obtained as a single light by combining two different complementary-color radiation emitted separately from two different light sources. As such an illuminator, it is preferable to use an illuminator having a system in which red light and blue-green light are emitted and combined, or a system in which two radiation obtained by allowing radiation to pass through a red filter and a blue-green filter are combined.

Alternatively, the radiation applied to the substrate by the illuminator can be obtained as flashing light by repeatedly and alternately flashing two different complementary-color radiation emitted from a single light source. As such an illuminator, it is preferable to use an illuminator comprising two kinds of filters for allowing two different color radiation to pass through, and these filters are preferably movable filters which are arranged in such a manner that an optical path is alternately intercepted by them. Thus, various kinds of illuminators can be used to inspect the surface of the substrate not only for defocusing but also dust and scratches. Particularly, illuminators can be useful to inspect the surface of the substrate for fine scratches produced in a step of flattening a surface of wafer and in a step of peeling resist.

The macro inspecting apparatus according to the present invention comprises: an illuminator for macro inspection which emits radiation; supporting means for supporting a substrate having a surface on which predetermined patterns are finely formed and to which the radiation is applied by the illuminator at a predetermined angle; and determining means for determining whether the predetermined patterns on the surface of the substrate are deformed or not by visually inspecting radiation diffracted by the finely patterned surface. The illuminator for macro inspection emits light including two different complementary-color radiation.

The surface of the substrate on which predetermined patterns are finely formed may function as a diffraction grating for diffracting and reflecting radiation when they are applied to the patterned surface. Where the patterns are uniformly formed on the substrate and there is no deformation in patterns, all the radiation applied to the patterned surface are diffracted and reflected in the same direction. Although it depends on visual angle, either one of two different complementary colors or a color obtained by synthesizing two different complementary colors appears on the whole of the patterned surface. Specifically, when the substrate (finely patterned surface) is rotated relative to the radiation, one of two different complementary colors, a color obtained by synthesizing two different complementary colors, the other of two different complementary colors, and a color obtained by synthesizing two different complementary colors appear in this order.

On the contrary, where there is some deformed patterns on the substrate due to defocusing, either one of two complementary colors appears on the whole of patterned surface while the other of two complementary colors appears locally on the surface. Unlike the above case, when the substrate (finely patterned surface) is rotated relative to the radiation, one of two complementary colors appears locally in the other color. For example, where the two complementary colors are red and blue green, the parts where red appears locally in blue green or blue green appears locally in red are deformed parts, so that deformed parts can be easily detected. Thus, a sharp contrast produced by complementary colors makes it much easier to visually inspect the surface of the substrate for deformed parts due to defocusing.

In the illuminator for macro inspection according to the present invention, two different high-contrast color radiation, especially radiation of two colors complementary to each other, are used. Since the finely-patterned surface of the substrate, to which radiation is applied, functions as a diffraction grating, the color of light diffracted by normal parts is the one color of a complementary color pair, and the color of light diffracted by deformed parts in the other color of the pair. Such complementary colors are vivid and have a sharp contrast, so that visual inspection can be easily conducted. Thus, the present invention makes it possible to visually inspect the surface of the substrate for deformed parts, even if there are only a few deformed parts. Experiments proved that the illuminator of the present invention made it possible to visually observe 5% (about 0.05 $\mu$m) of changes in a resist pattern.

Thus, the present invention makes it possible to visually inspect a surface of a substrate for deformed parts on a process line even if there are only a few deformed parts. Therefore, a failure of production equipment can also be detected at an early stage, so that defective items can be minimized and yielding loss can be reduced by recycling the defective items.

DESCRIPTION OF THE PREFERRED EMBODIMENTS

Next, embodiments of the illuminator for macro inspection, macro inspecting apparatus and method according to the present invention will hereinafter be described in detail with reference to the accompanying drawings.

Figure 1:
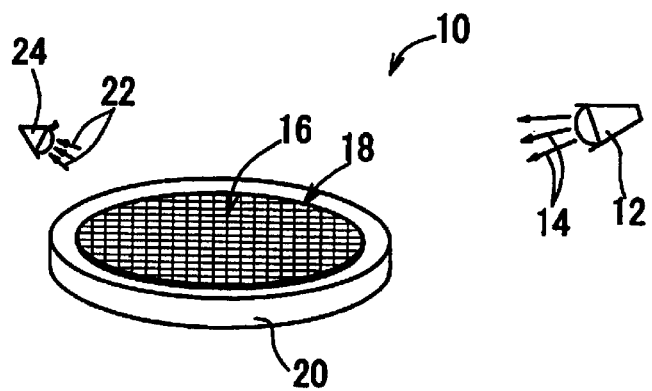
FIG. 1 is a schematic diagram of the macro inspecting apparatus of the present invention.

As shown in FIG. 1, a macro inspecting apparatus 10 comprises: an illuminator 12 for macro inspection which emits radiation; supporting means 20 for supporting a substrate 18 having a surface 16 on which predetermined patterns are finely formed and to which the radiation 14 are applied by the illuminator 12 at a predetermined angle; and determining means 24 for determining whether or not the predetermined patterns on the surface 16 is deformed due to defocusing by visually inspecting radiation 22 diffracted by the finely patterned surface 16. The illuminator 12 for macro inspection emits light including two different complementary-color radiation. The light from the illuminator is required to be able to produce interference and diffraction but not required to be coherent.

Figure 2:
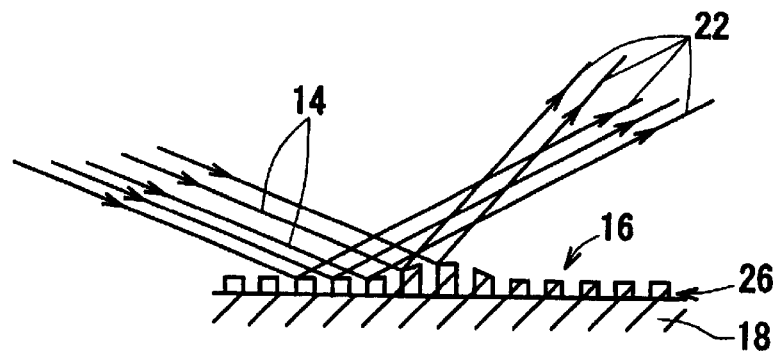
FIG. 2 is a schematic diagram showing one embodiment of the illuminator for macro inspection according to the present invention.

Examples of the substrate 18 having the surface 16 on which predetermined patterns are formed may include such wafers as silicon wafers, glass substrates, and the like. Examples of the. finely-patterned surface 16 of the substrate 18 may include resist patterns 26 obtained by forming a resist layer into a predetermined pattern by a photolithography method as shown in FIG. 2, and a patterned surface obtained by etching a silicon layer and the like laminated on the substrate such as a wafer and a glass substrate in accordance with the above resist pattern. Preferably, the resist pattern 26 has a pitch of about 3 $\mu$m or less in order to diffract the radiation.

The substrate 18 is placed on the supporting means 20 such as a rotary table or a fixed table in such a manner that the space between the substrate 18 and the illuminator 12 and the angle which incident light from the illuminator 12 forms with the substrate 18 are kept constant. Where the supporting means 20 is rotatable, it is preferable that the presence or absence of deformed parts due to defocusing is detected by rotating the means 20 by 90 degrees to apply the radiation 14 to the surface from the different directions, and then obtaining the diffracted radiation 22.

The illuminator 12 for macro inspection is the device for emitting radiation 14 whose colors are complementary to each other. As far as the radiation 14 include complementary-color radiation, it may partly include radiation of other colors. Preferably, the illuminator 12 for emitting complementary color radiation 14 emits light including two different complementary-color radiation 14 from a single light source. There are many combinations of two different colors complementary to each other. Examples of complementary color pairs are red and blue green, yellow and blue, green and brown, and the like. The colors of radiation 14 are not necessarily complementary to each other, but they may be high-contrast colors close to complementary colors. The most preferable complementary color pair is red and blue green in terms of contrast effect. A combination of two different complementary colors produces a sharper contrast than any other combination of two colors, and gives a glaring and sharp impression to human eyes. One of two complementary colors can be visually distinguished from the other. As such an illuminator, it is preferable to use a halogen lamp having a color temperature of 1500K to 3500K and including red light with a wavelength of 677 nm and blue green light with a wavelength of 495 nm. Particularly, a halogen lamp having a color temperature of 2200K is preferable. Since spectral intensity of red light is stronger than that of blue green light in the halogen lamp having a color temperature of 2200K, red and blue green are perceived as substantially equal brightness of colors when they are visually inspected, so that color discrimination is much more easier.

Preferably, the illuminator 12 for macro inspection is located in a manner that the light 14 is incident on the substrate 18 from the illuminator 12 at the angle of about 15 degrees, for example. In addition, the distance, between the illuminator 12 and the substrate 18 is preferably about 500 mm for example. If the illuminator 12 is too far away from the substrate 18, the illumination intensity is reduced and the contrast of the diffracted radiation is lowered, so that some defocusing defects are left unnoticed on the substrate. On the contrary, if the illuminator 12 is too near to the substrate 18, the illumination intensity becomes too high, which causes the deterioration of eyesight of a person. who visually inspects the diffracted radiation 22. Moreover, the illuminator 12 applies the light to a limited part in this case, which makes it difficult to visually inspect the surface of the substrate for deformed parts. Experiments proves that preferable illumination intensity is 300 Lx or more. Under the above conditions, preferable output of the halogen lamp is about 200 W.

On the other hand, the distance between the substrate 18 and a person who visually inspects the diffracted radiation 22 is preferably about 700 mm, for example. If he/she comes too near the substrate 18, his/her view becomes narrower. On the contrary, if he/she is far away from the substrate 18, the contrast of diffracted radiation becomes worse. It is preferable that the person inspects the diffracted radiation 22 at an easy-to-see angle, which can be selectively predetermined by experiments.

The radiation 14 applied to the substrate 18 by the illuminator 12 are reflected and diffracted on the surface 16 on which predetermined patterns are formed. Where there are no deformed parts due to defocusing on the surface 16, all the radiation will be reflected and diffracted in the same direction by the whole surface, so that the colors of radiation 22 which are visually inspected are substantially the same. When the substrate rotates 45 degrees on the supporting means 20, the color of the light turns from one of two different complementary colors into a mixed color. When the substrate rotates 90 degrees, the color of the light turns into the other color of two different complementary colors.

On the contrary, where there are some deformed parts due to defocusing on the surface 16, the radiation 22 diffracted by the surface 16 are the same color, namely one of two different complementary colors, except for the radiation diffracted by the deformed parts of the surface. The radiation 22 diffracted by the deformed parts are turned into the other color of two different complementary colors. Assuming that these two complementary colors are, for example, red and blue green and the radiation 22 diffracted by normal surface is blue green, the radiation 22 diffracted by the deformed parts of the surface is red. In this case, when the substrate 18 rotates 90 degrees, the radiation diffracted by normal surface turn into red, and the radiation diffracted by the deformed parts of the surface turn into blue green. Thus, visual inspection of diffracted radiation 22 makes it possible to detect the deformed parts such as defocusing over the surface of the substrate.

While an embodiment of the present invention has thus been described, it should be understood that the present invention be not limited to the above embodiment.

Figure 3:
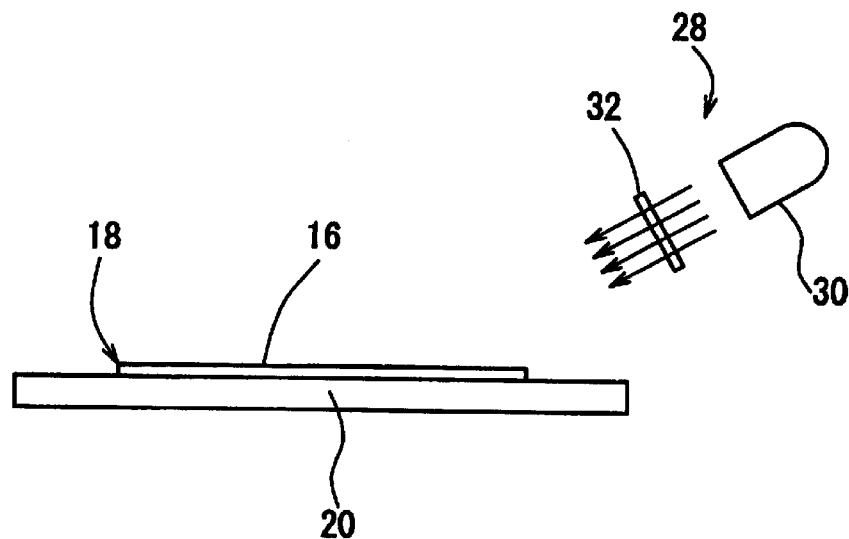
FIG. 3 is a schematic diagram showing another embodiment of the illuminator for macro inspection according to the present invention.

For example, as shown in FIG. 3, the illuminator 28 for macro inspection may comprise a single light source 30 and a filter 32 for allowing two different complementary-color radiation to pass through. The light source 30 is not limited to halogen lamps and the like, but it may be the device for emitting colorless light or light including two different complementary-color radiation, which can be selected by the filter 32. As the filter 32, usable is a yellow broad band filter of a wide wavelength range, through which both red and blue green radiation is allowed to pass.

Figure 4:
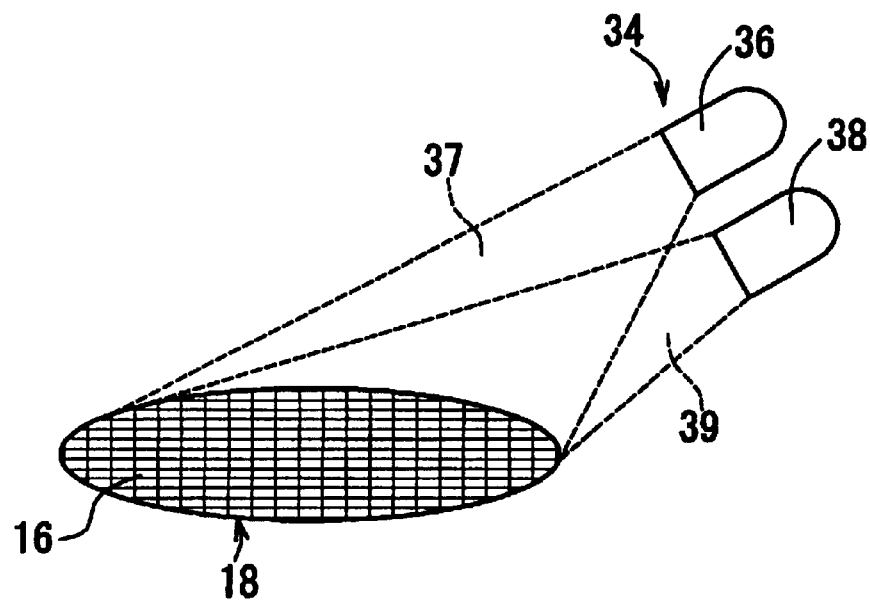
FIG. 4 is a schematic diagram showing still another embodiment of the illuminator for macro inspection according to the present invention.

Alternatively, the illuminator 34 for macro inspection may comprise two light sources 36 and 38 for separately emitting light including two different complementary-color radiation 37 and 39, as shown in FIG. 4. The complementary color radiation 37 and 39, which are emitted from the two light sources 36 and 38 of the illuminator 34, are combined to form one light when they reach at least the surface of the substrate 18 or before they reach the substrate 18. For example, the illuminator 34 may comprise a light source for emitting red light and a light source for emitting blue green light.

Figure 5:
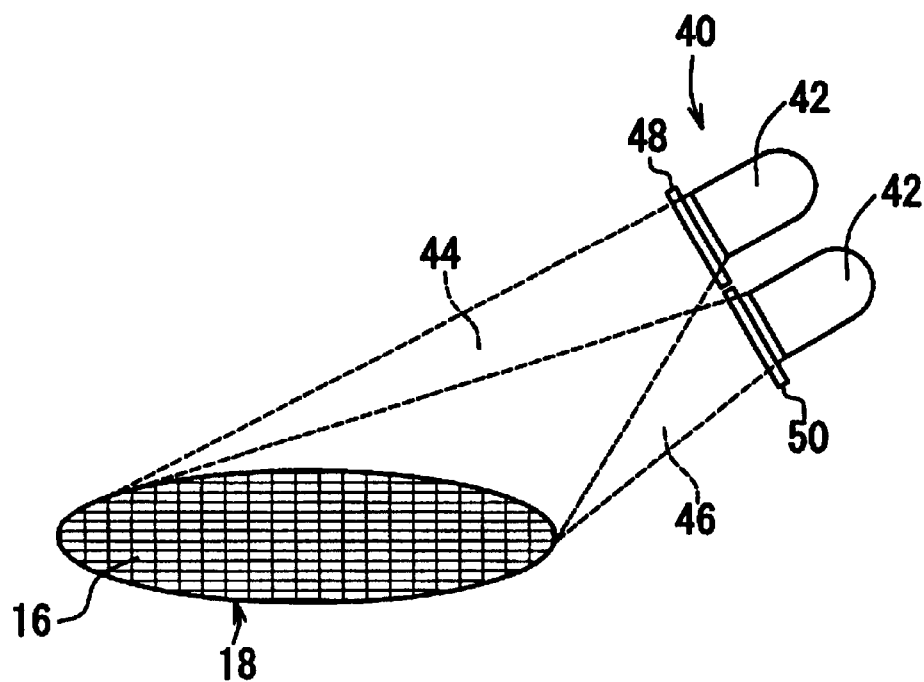
FIG. 5 is a schematic diagram showing a further embodiment of the illuminator for macro inspection according to the present invention.

Alternatively, the illuminator 40 for macro inspection may comprise two light sources 42 and two kinds of filters 48 and 50 for allowing two different complementary-color radiation 44 and 46 to separately pass through, as shown in FIG. 5. The complementary color radiation 44 and 46, which are emitted from the two light sources 42 of the illuminator 40 are combined to form one light when they reach at least the surface of the substrate 18 or before they reach the substrate 18. For example, radiation is allowed to pass through the red filter and the blue green filter to obtain red and blue green radiation. Then these two different color radiation is combined to form one light.

Figure 6:
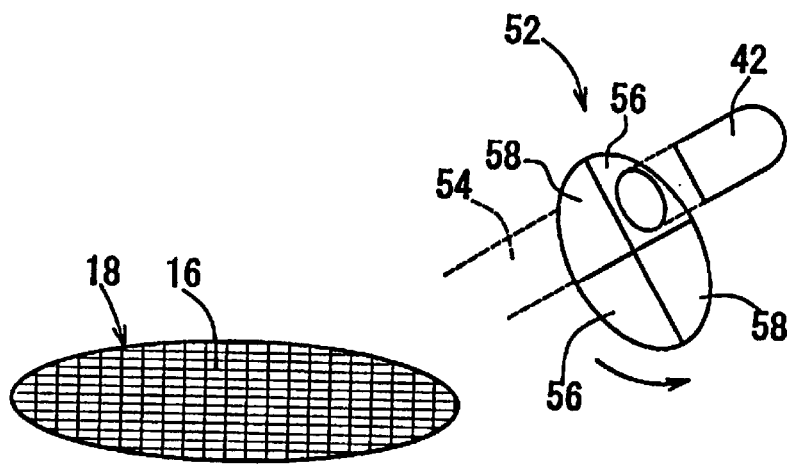
FIG. 6 is a schematic diagram showing a still further embodiment of the illuminator for macro inspection according to the present invention.

Alternatively, the light 54 applied to the substrate 18 by the illuminator 52 can be obtained as flashing light by repeatedly and alternately flashing two different complementary-color radiation emitted from a single light source 42, as shown in FIG. 6. In such illuminator 52, it is preferable that two filters 56 and 58 which allow light including two complementary-color radiation 54 to separately pass through are placed so as to intercept the optical path of radiation 54. Preferably, two filters 56 and 58 can be rotated around the axis so as to be alternately inserted into the optical path of radiation 54. The filters 56 and 58 can not only be arranged to form a geometry of a disc, but they can also be placed alternately in a line. When flashing radiation is visually inspected, they are recognized as a continuous light by persistence of vision. As in the case described above, different color is locally observed when there are deformed parts due to defocusing. Therefore, deformed parts can be thus detected by using the persistence of vision.

In any of these illuminators for macro inspection, the finely patterned surface of the substrate functions as a diffraction grating. Since a contrast difference between radiation diffracted by normal parts and radiation diffracted by deformed parts is caused by slight displacement of patterns in microns, deformed parts due to defocusing can be detected. Particularly, radiation emitted form the illuminator of the present invention includes two different complementary-color radiation, so that maximum contrast difference can be obtained.

When deformed parts such as defocusing are inspected at a resist stage by using the illuminator for macro inspection, radiation of short wavelengths are cut and used so as not to expose the resist to the radiation from the illuminator. Since an inspection for defocusing may often be conducted at a manufacturing location, it is preferable that short wavelengths in a photosensitive range of photosensitive resin such as resist are previously cut by an optical filter for use as wavelengths of the illuminator.

Figure 7:
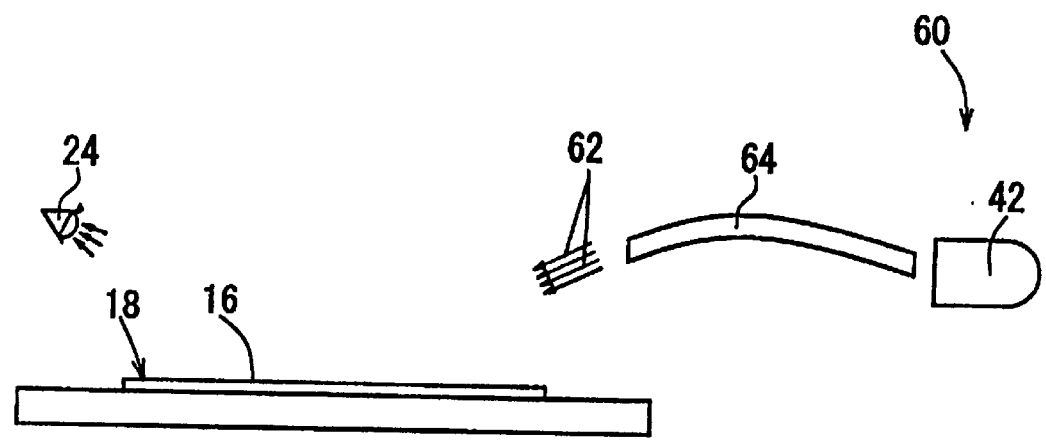
FIG. 7 is a schematic diagram showing another embodiment of the macro inspecting apparatus of the present invention.

Preferably, the illuminator for macro inspection is placed near the supporting means on which the substrate is placed, so that the illuminator can apply light directly to the surface of the substrate. However, where the illuminator cannot apply light directly to the substrate because space for the inspecting apparatus is limited, a light conductor 64 for conducting radiation 62 emitted from the light source 42 to the substrate 18 can be placed between the illuminator 60 and the substrate 18, as shown in FIG. 7. As the light conductor 64, optical fiber is most preferably used. However, a transparent plate can be also used. By using the light conductor 64 such as optical fiber having flexibility, various conditions such as illumination angle can be easily set up. As the illuminator 60 for macro inspection, various illuminators described above can be used.

While the illuminator for macro inspection, macro inspecting apparatus and method according to the present invention have thus been described with reference to the accompanying drawings, it should be understood that the present invention be not limited to these embodiments.

For example, the illuminator for macro inspection according to the present invention enables the visual inspection for defocused parts. However, by the combination of conventional techniques, the illuminator of the present invention enables automatic inspection. For example, colors of radiation can be automatically inspected by using image processing technique or by using an optoelectronic transducer which converts changes in colors of diffracted radiation into electric signal. By such combinations of techniques, higher inspection accuracy can be achieved.

The illuminator for macro inspection and the macro inspecting apparatus according to the present invention can be used for inspect the surface of the substrate not only for defocused parts but also for dust and scratches on the surface of the substrate. In addition, the illuminator and the inspecting apparatus according to the present invention can be used to inspect the surface of the substrate for defects such as fine scratches produced in a step of flattening a surface of wafer and in a step of peeling resist.

Additionally, it is preferable to use a mirror-finished reflector having no dimples as a reflector for the light source of the halogen lamp. Thus, the present invention is intended to embrace various improvements, modifications, and variations made on the basis of knowledge of those skilled in the art without departing from the scope of the invention.

EXAMPLES

Example 1

Figure 8:
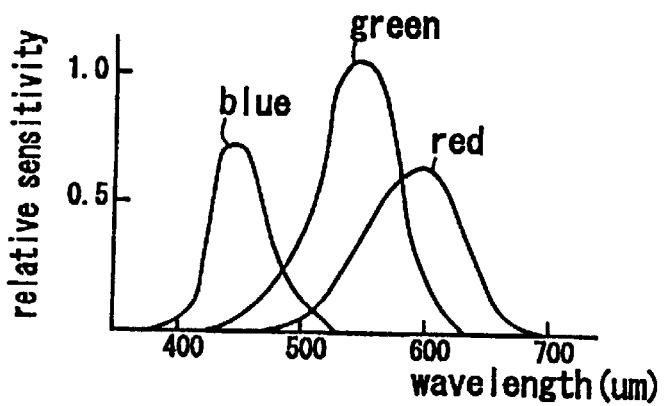
FIG. 8 is a curve showing the sensitivity of cone of a human eye.

First, a light source which is suitably used for visual inspection for defocused parts was selected. Since the intensity that human can perceive is an integral value obtained by spectral luminance efficiency shown in FIG. 8 and spectral characteristic of the light source, attention was directed to red (677 nm) and blue green (495 nm), which are complementary to each other within a wavelength range necessary for visual inspection. The contrast effect of these complementary colors is the highest when brightnesses of these two colors are equal. (Kirschman's law) Metal halide, halogen, and xenon lamps are tested by using a spectrum of each lamp to determine which lamp is the most suitable as a light source for equalizing lightnesses of red light and blue green light. The results showed that the halogen lamp having a color temperature of 2200K was the most suitable light source.

Example 2

Figure 9:
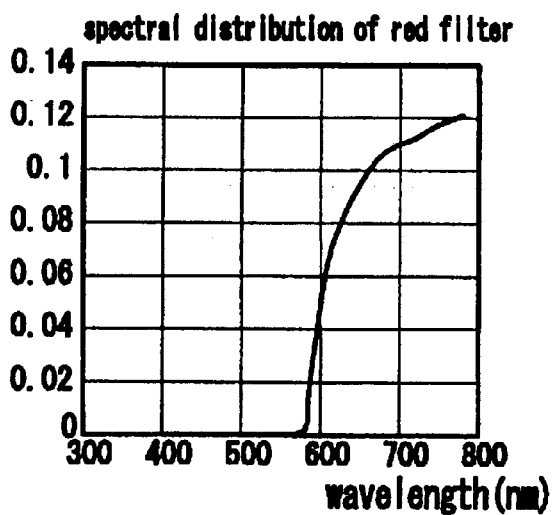
FIG. 9 is a diagram showing spectral characteristics of red, green and yellow filters used in experiments.
Figure 9:
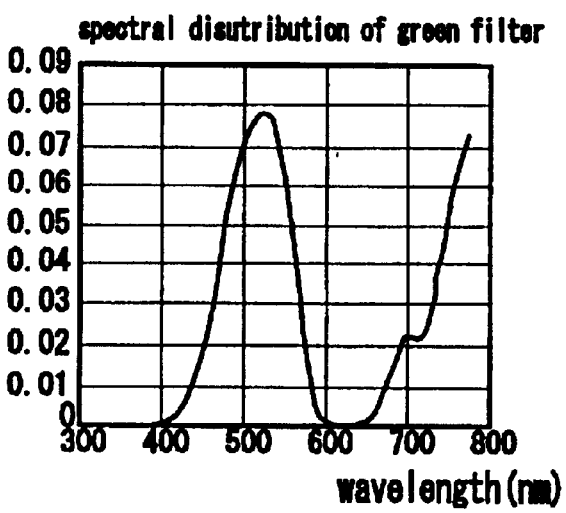
Figure 9:
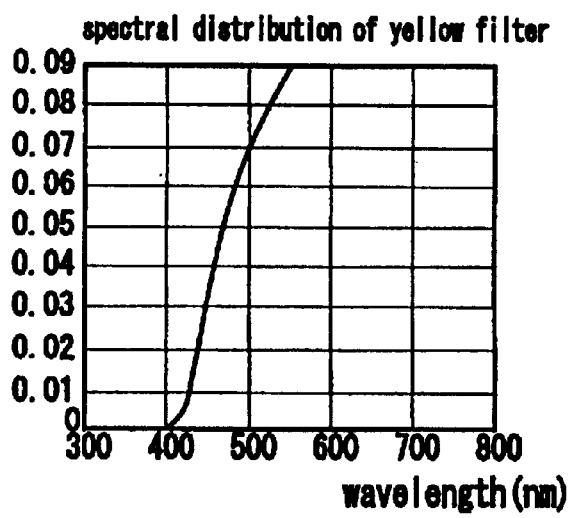

In this embodiment, visual inspections for defocused parts were conducted by using a halogen lamp (AC100V-200 W) having a color temperature of 3050K and three filters of red, green and yellow (red and green) which have spectral distributions shown in FIG. 9, and results of the inspections were compared. The illuminances on the wafer were equally adjusted by using an ND (neutral density) filter. The wafer was slightly tilted with respect to a photomask with a pitch of 0.88 µm and exposed to light to form defocused parts on it.

The result showed that a synergistic effect of contrast between normal parts and deformed parts (a visible difference in the intensity of diffracted radiation) and color difference (difference in frequency between red light diffracted by the normal part and blue green light diffracted by the deformed parts, or vise versa) made it possible to clearly observe defocused parts of resist patterns having a pitch of 0.88 µm (in a range of −0.05 µm to +0.05 µm). This result satisfied the demand for detection sensitivity necessary in mass-production.

Example 3

Quantitative tests were conducted to determine how much amount of the change in resist patterns (namely, how much amount of defocused patterns) is necessary to conduct a visual inspection. In the tests, a test pattern with a pitch of 0.8 µm, which is considered to be equivalent to a uniform diffraction grating, was used to form a normal wafer and a wafer containing defocused parts by increasing the level of a stage to +0.7 µm and to +1.4 µm with reference to the level of the stage where correct focus was obtained by a focus offset function of the stepper. The visual inspections were conducted by using a halogen lamp having a color temperature of 3050K and comprising a mirror-finished reflector, two flat convex lenses, an illumination system aperture, and a broad band yellow filter which cuts a wavelength of 520 nm or less.

Figure 10:
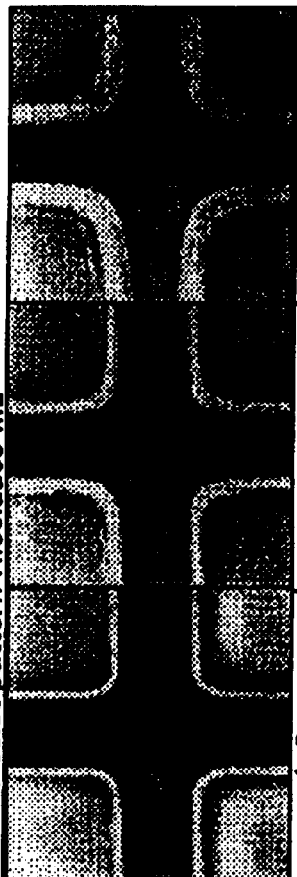
FIG. 10 is a diagram showing a relation between the amount of deviation of a resist pattern caused by defocusing and visual inspection.

Luminances and chromaticities of normal parts (+0.7 µm) and deformed parts (+1.4 µm) were measured using TOPCON BM-5A luminance meter. Results of measurements were shown in FIG. 10. In FIG. 10, white lines indicate side walls of the resist pattern. It is clear from the FIG. 10. that the side walls becomes wider due to defocused parts.

Figure 11:
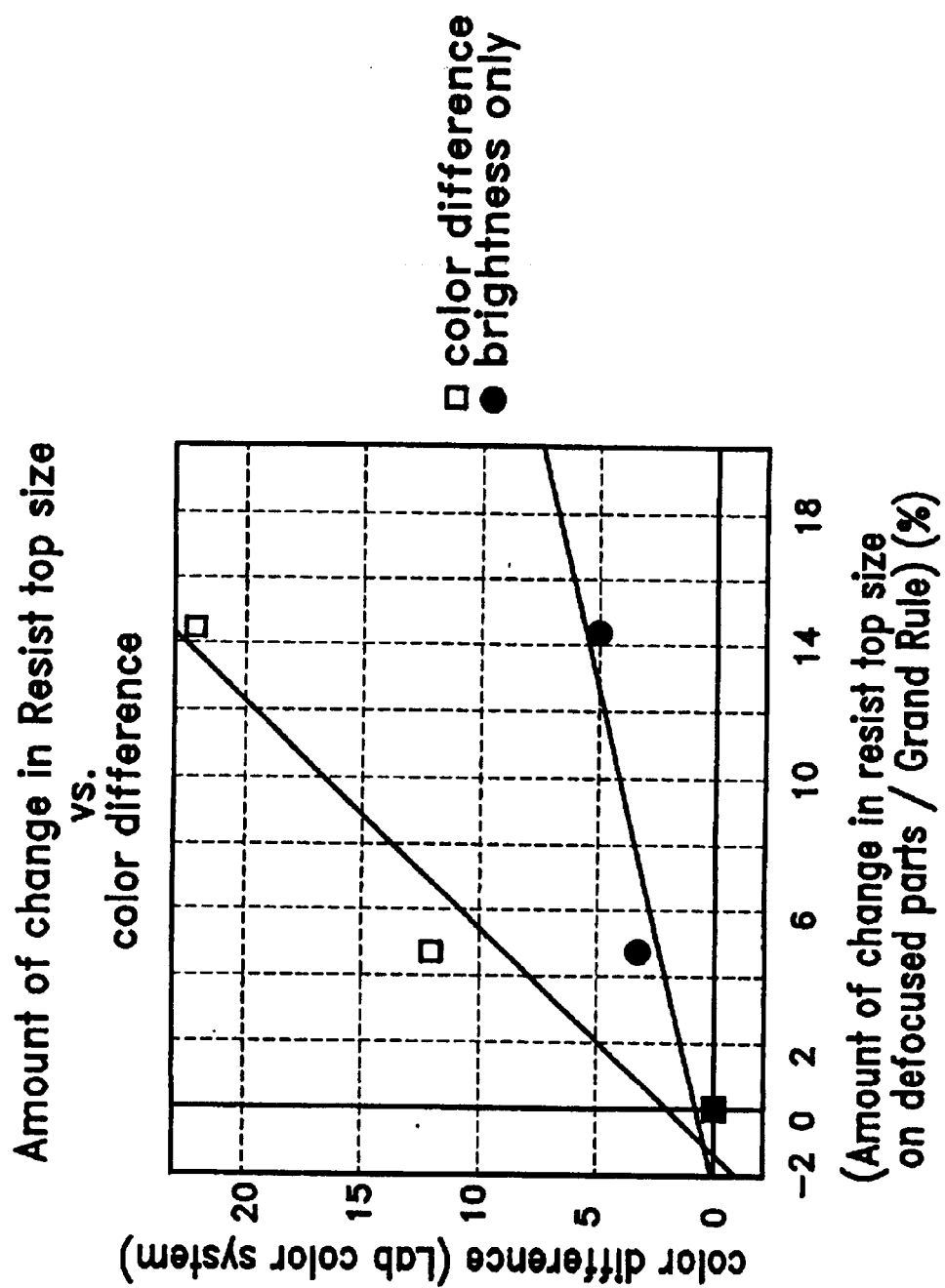
FIG. 11 is a diagram showing a relation between the amount of the change in resist top size of a resist pattern and color differences.

FIG. 11 shows a relationship between the amount of change in resist top sizes of a resist pattern and color difference. The amount of change in a width of a resist line, which exerts influence on a process, is said to be about 0.05% of the line width. It is difficult to visually inspect the substrate for the defocused parts only by using a contrast between light and shade. However, by using color differences, it is four times easier to visually inspect the substrate for defocused parts. The illuminator of the present invention made it possible to observe 0.04 µm (5%) of changes in a resist pattern.

What is claimed is:

1. An apparatus for inspecting a workpiece having a fine feature pattern formed thereon comprising:

rotatable means for supporting said workpiece and rotating said workpiece about an azimuthal angle; and an illuminator having at least one radiation source for directing bright-field illumination in at least two high contrast spectrum regions at said workpiece, wherein at a given azimuthal angle the workpiece diffracts the radiation so that radiation reflected from a defect-free area of the pattern is in a first spectrum region and radiation reflected from a defect in the pattern is in a second spectrum region, and at a different azimuthal angle the workpiece diffracts the radiation so that radiation reflected from a defect-free area of the pattern is in the second spectrum region and radiation reflected from a defect in the pattern is in the first spectrum region.

2. The apparatus according to claim 1, wherein the two high contrast spectrum regions are complementary to each other.

3. The apparatus according to claim 1, wherein the illuminator comprises a single light source for emitting radiation including said two high contrast spectrum regions.

4. The apparatus for macro inspection according to claim 3, wherein said two high contrast spectrum regions are red and blue-green radiation.

5. The apparatus for macro inspection according to claim 4, wherein said red radiation has a stronger spectral intensity than said blue-green radiation.

6. The apparatus for macro inspection according to claim 3, wherein said single light source is a halogen lamp having a color temperature of 1500 K to 3500 K and including red light with a wavelength of 677 nm and blue-green light with a wavelength of 495 nm.

7. An apparatus for inspecting a workpiece having a fine feature pattern formed thereon, comprising;

rotatable means for supporting said workpiece and rotating said workpiece about an azimuthal angle;

an illuminator having at least one radiation source for directing bright-field illumination in at least two high contrast spectrum regions at said workpiece; and spectrum responsive detection means for detecting reflected radiation as a function of workpiece azimuthal angle, wherein at a given azimuthal angle the workpiece diffracts the radiation so that radiation reflected from a defect-free area of the pattern is in a first spectrum region and radiation reflected from a defect in the pattern is in a second spectrum region, and at a different azimuthal angle the workpiece diffracts the radiation so that radiation reflected from a defect-free area of the pattern is in the second spectrum region and radiation reflected from a defect in the pattern is in the first spectrum region, whereby the defect may be detected.

8. The apparatus according to claim 7, wherein the two high contrast spectrum regions are complementary to each other.

9. The apparatus according to claim 7, wherein the illuminator comprises a single light source for emitting radiation including said two high contrast spectrum regions.

10. The apparatus according to claim 9, wherein said two high contrast spectrum regions are red and blue-green radiation.

11. The apparatus according to claim 10, wherein said red radiation has a stronger spectral intensity than said blue-green radiation.

12. The apparatus according to claim 9, wherein said single light source is a halogen lamp having a color temperature of 1500 K to 3500 K and including red light with a wavelength of 677 nm and blue-green light with a wavelength of 495 nm.

13. The apparatus according to claim 7, wherein the illuminator comprises:

two light sources; and two kinds of filters for allowing radiation in the two high contrast spectrum regions to separately pass through.

14. The apparatus according to claim 13, wherein said two kinds of filters are a red filter and a blue-green filter.

15. The apparatus according to claim 7, wherein the illuminator comprises:

a single light source; and a filter of a wide wavelength range for allowing radiation including two different high contrast spectrum regions to pass through.

16. The apparatus according to claim 15, wherein said filter is a yellow filter of a wide wavelength range.

17. The apparatus according to claim 7, further comprising a light guide for conducting light emitted from the illuminator to the workpiece.

18. A macro inspecting method, comprising the steps of:
applying bright-field illumination including radiation in two different high contrast spectrum regions to a surface of a substrate having a pattern formed thereon; and
inspecting radiation diffracted by said pattern to detect a defect therein,
wherein the substrate diffracts the radiation so that radiation reflected from a defect-free area of the pattern is in a first spectrum region and radiation reflected from a defect in the pattern is in a second spectrum region.

19. A method according to claim 18, wherein said inspecting step further comprises rotating the substrate about an azimuthal angle, wherein at a given azimuthal angle the pattern diffracts the radiation so that a defect-free area of the pattern reflects the radiation in the first spectrum region and a defect in the pattern reflects the radiation in the second spectrum region, and at a different azimuthal angle the pattern diffracts the radiation so that a defect-free area of the pattern reflects the radiation in the second spectrum region and a defect in the pattern reflects the radiation in the first spectrum region.

20. A method according to claim 18, wherein said inspecting step is performed using an automated image processing technique.

\* \* \* \* \*